(12) United States Patent
Hillstead et al.

(10) Patent No.: US 7,803,103 B2
(45) Date of Patent: Sep. 28, 2010

(54) METHODS AND APPARATUS FOR INTRAOCULAR BRACHYTHERAPY

(75) Inventors: Richard A Hillstead, Duluth, GA (US); Charles E. Larsen, Cumming, GA (US); Roelof Trip, Sawanee, GA (US); Cory S. Anderson, Apharetta, GA (US)

(73) Assignee: NeoVista Inc., Fremont, CA (US)

( * ) Notice: Subject to any disclaimer, the term of this patent is extended or adjusted under 35 U.S.C. 154(b) by 379 days.

(21) Appl. No.: 11/559,958

(22) Filed: Nov. 15, 2006

(65) Prior Publication Data

US 2007/0118010 A1 May 24, 2007

Related U.S. Application Data

(63) Continuation-in-part of application No. 11/228,030, filed on Sep. 15, 2005, now Pat. No. 7,563,222, which is a continuation-in-part of application No. 11/056,763, filed on Feb. 11, 2005, now Pat. No. 7,744,520.

(60) Provisional application No. 60/736,783, filed on Nov. 15, 2005, provisional application No. 60/554,001, filed on Feb. 12, 2004.

(51) Int. Cl.
*A61M 36/00* (2006.01)
*A61N 5/00* (2006.01)

(52) U.S. Cl. ........................................... 600/7

(58) Field of Classification Search .................. 600/1–8
See application file for complete search history.

(56) References Cited

U.S. PATENT DOCUMENTS

| | | | |
|---|---|---|---|
| 839,061 A | 12/1906 | Farjas | |
| 2,517,568 A | 8/1950 | Hissong | |
| 2,559,793 A | 7/1951 | Pregel | |
| 4,198,570 A | 4/1980 | McHugh et al. | |
| 4,584,991 A | 4/1986 | Tokita et al. | |
| 4,662,869 A | 5/1987 | Wright | |
| 4,720,286 A | 1/1988 | Bailey et al. | |
| 4,846,172 A | 7/1989 | Berlin | |
| 4,861,520 A | 8/1989 | Van't Hooft et al. | |
| 4,891,165 A | 1/1990 | Suthanthiran | |
| 4,921,327 A | 5/1990 | Zito | |
| 4,957,476 A | 9/1990 | Cano | |

(Continued)

FOREIGN PATENT DOCUMENTS

DE 19933284 1/2001

(Continued)

OTHER PUBLICATIONS

Dig. J Opthalmol, "Development in Retinal Cell Transplants", 2001, vol. 7(2) From: http://www.medscape.com/viewarticle/408963_print.

(Continued)

*Primary Examiner*—John P Lacyk
(74) *Attorney, Agent, or Firm*—Cook Alex Ltd.

(57) ABSTRACT

Methods and apparatus for intraocular brachytherapy are disclosed in which a cannula is introduced into the eye for delivery of radiation to a target tissue. Techniques for properly locating the cannula with respect to the target tissue, for protecting non-target tissue, for regulating heat generated by x-ray emitters, and for combining therapies are disclosed.

8 Claims, 6 Drawing Sheets

U.S. PATENT DOCUMENTS

| | | |
|---|---|---|
| 4,976,720 A | 12/1990 | Machold et al. |
| 4,996,159 A | 2/1991 | Glaser |
| 5,084,001 A | 1/1992 | Van'tHooft et al. |
| 5,123,902 A | 6/1992 | Muller et al. |
| 5,129,895 A | 7/1992 | Vassiliadis et al. |
| 5,141,487 A | 8/1992 | Liprie |
| 5,147,282 A | 9/1992 | Kan |
| 5,183,455 A | 2/1993 | Hayman et al. |
| 5,199,939 A | 4/1993 | Dake et al. |
| 5,203,353 A | 4/1993 | Easley et al. |
| 5,257,988 A | 11/1993 | L'Esperance, Jr. |
| 5,267,960 A | 12/1993 | Hayman et al. |
| 5,282,781 A | 2/1994 | Liprie |
| 5,290,585 A | 3/1994 | Elton |
| 5,322,499 A | 6/1994 | Liprie |
| 5,329,923 A | 7/1994 | Lundquist |
| 5,342,283 A | 8/1994 | Good |
| 5,354,257 A | 10/1994 | Roubin et al. |
| 5,408,874 A | 4/1995 | Fleck, Sr. et al. |
| 5,422,926 A | 6/1995 | Smith et al. |
| 5,425,730 A | 6/1995 | Luloh |
| 5,426,662 A | 6/1995 | Mefferd et al. |
| 5,431,907 A | 7/1995 | Abelson et al. |
| 5,487,725 A | 1/1996 | Peyman |
| 5,503,613 A | 4/1996 | Weinberger |
| 5,503,614 A | 4/1996 | Liprie |
| 5,528,651 A | 6/1996 | Leksell et al. |
| 5,556,389 A | 9/1996 | Liprie |
| 5,570,408 A | 10/1996 | Gibson |
| 5,575,749 A | 11/1996 | Liprie |
| 5,596,011 A | 1/1997 | Repine et al. |
| 5,618,266 A | 4/1997 | Liprie |
| 5,624,372 A | 4/1997 | Liprie |
| 5,624,437 A | 4/1997 | Freeman et al. |
| 5,637,073 A | 6/1997 | Freire |
| 5,651,783 A | 7/1997 | Reynard |
| 5,670,558 A | 9/1997 | Onishi et al. |
| 5,688,220 A | 11/1997 | Verin et al. |
| 5,707,332 A | 1/1998 | Weinberger |
| 5,713,828 A | 2/1998 | Coniglione |
| 5,728,042 A | 3/1998 | Schwager |
| 5,729,583 A | 3/1998 | Tang et al. |
| 5,738,677 A | 4/1998 | Colvard et al. |
| 5,772,642 A | 6/1998 | Ciamacco, Jr. et al. |
| 5,782,740 A | 7/1998 | Schneiderman |
| 5,797,889 A | 8/1998 | Steinman |
| 5,807,231 A | 9/1998 | Liprie |
| 5,830,173 A | 11/1998 | Avery et al. |
| 5,833,593 A | 11/1998 | Liprie |
| 5,836,882 A | 11/1998 | Frazin |
| 5,854,822 A | 12/1998 | Chornenky et al. |
| 5,855,546 A | 1/1999 | Hastings et al. |
| 5,857,956 A | 1/1999 | Liprie |
| 5,863,284 A | 1/1999 | Klein |
| 5,865,720 A | 2/1999 | Hastings et al. |
| 5,882,291 A | 3/1999 | Bradshaw et al. |
| 5,885,279 A | 3/1999 | Bretton |
| 5,899,882 A | 5/1999 | Waksman et al. |
| 5,904,144 A | 5/1999 | Hammang et al. |
| 5,913,813 A | 6/1999 | Williams et al. |
| 5,924,974 A | 7/1999 | Loffler |
| 5,928,130 A | 7/1999 | Schmidt |
| 5,947,958 A | 9/1999 | Woodard et al. |
| 5,957,829 A | 9/1999 | Thornton |
| 5,976,106 A | 11/1999 | Verin et al. |
| 5,984,853 A | 11/1999 | Smith |
| 6,004,269 A | 12/1999 | Crowley et al. |
| 6,004,279 A | 12/1999 | Crowley et al. |
| 6,019,718 A | 2/2000 | Hektner |
| 6,024,690 A | 2/2000 | Lee et al. |
| 6,030,333 A | 2/2000 | Sioshansi et al. |
| 6,033,357 A | 3/2000 | Ciezki et al. |
| 6,036,631 A | 3/2000 | McGrath et al. |
| 6,041,252 A | 3/2000 | Walker et al. |
| 6,050,930 A | 4/2000 | Teirstein |
| 6,053,858 A | 4/2000 | Bueche et al. |
| 6,059,713 A | 5/2000 | Urick et al. |
| 6,059,752 A | 5/2000 | Segal |
| 6,059,828 A | 5/2000 | Peyman |
| 6,069,938 A | 5/2000 | Chornenky et al. |
| 6,071,227 A | 6/2000 | Popowski et al. |
| 6,074,338 A | 6/2000 | Popowski et al. |
| 6,093,142 A | 7/2000 | Ciamacco, Jr. |
| 6,095,966 A | 8/2000 | Chornenky et al. |
| 6,099,457 A | 8/2000 | Good |
| 6,099,499 A | 8/2000 | Ciamacco, Jr. |
| 6,102,844 A | 8/2000 | Ravins et al. |
| 6,106,454 A | 8/2000 | Berg et al. |
| 6,108,402 A | 8/2000 | Chornenky |
| 6,111,932 A | 8/2000 | Dinsmore |
| 6,117,480 A | 9/2000 | Spallek et al. |
| 6,134,294 A | 10/2000 | Gibbs |
| 6,142,994 A | 11/2000 | Swanson et al. |
| 6,146,322 A | 11/2000 | Papirov et al. |
| 6,149,574 A | 11/2000 | Trauthen et al. |
| 6,149,931 A | 11/2000 | Schwartz et al. |
| 6,159,140 A | 12/2000 | Loeffler et al. |
| 6,162,165 A | 12/2000 | Apple et al. |
| 6,163,947 A | 12/2000 | Coniglione |
| 6,164,281 A | 12/2000 | Zhao |
| 6,179,768 B1 | 1/2001 | Loffler et al. |
| 6,181,770 B1 | 1/2001 | Ciravolo et al. |
| 6,183,410 B1 | 2/2001 | Jacobsen et al. |
| 6,195,411 B1 | 2/2001 | Dinsmore |
| 6,196,963 B1 | 3/2001 | Williams |
| 6,198,804 B1 | 3/2001 | Dinsmore |
| 6,203,524 B1 | 3/2001 | Burney et al. |
| 6,210,312 B1 | 4/2001 | Nagy |
| 6,210,315 B1 | 4/2001 | Andrews et al. |
| 6,213,932 B1 | 4/2001 | Schmidt |
| 6,224,536 B1 | 5/2001 | Pike |
| 6,231,494 B1 | 5/2001 | Verin et al. |
| 6,234,951 B1 | 5/2001 | Hastings |
| 6,241,651 B1 | 6/2001 | Smith et al. |
| 6,245,047 B1 | 6/2001 | Feda et al. |
| 6,258,019 B1 | 7/2001 | Verin et al. |
| 6,264,599 B1 | 7/2001 | Slater et al. |
| 6,273,850 B1 | 8/2001 | Gambale et al. |
| 6,283,910 B1 | 9/2001 | Bradshaw et al. |
| 6,283,911 B1 | 9/2001 | Keren |
| 6,284,751 B1 | 9/2001 | Aiello et al. |
| 6,285,735 B1 | 9/2001 | Sliski et al. |
| 6,289,079 B1 | 9/2001 | Chornenky et al. |
| 6,293,899 B1 | 9/2001 | Sioshansi et al. |
| 6,299,054 B1 | 10/2001 | Gibbs, Jr. |
| 6,301,328 B1 | 10/2001 | Sliski et al. |
| 6,302,581 B1 | 10/2001 | Sliski et al. |
| 6,306,074 B1 | 10/2001 | Waksman et al. |
| 6,312,374 B1 | 11/2001 | von Hoffmann |
| 6,312,393 B1 | 11/2001 | Abreu |
| 6,320,932 B2 | 11/2001 | Dinsmore |
| 6,320,935 B1 | 11/2001 | Shinar et al. |
| 6,338,709 B1 | 1/2002 | Geoffrion et al. |
| 6,347,244 B1 | 2/2002 | Dubnack |
| 6,352,501 B1 | 3/2002 | Urick |
| 6,354,989 B1 | 3/2002 | Nudeshima |
| 6,359,963 B1 | 3/2002 | Cash |
| 6,377,846 B1 | 4/2002 | Chornenky et al. |
| 6,378,526 B1 | 4/2002 | Bowman et al. |
| 6,387,035 B1 | 5/2002 | Jung, Jr. et al. |
| 6,391,026 B1 | 5/2002 | Hung et al. |
| 6,395,294 B1 | 5/2002 | Peyman |
| 6,397,849 B1 | 6/2002 | Bowman et al. |
| 6,402,676 B2 | 6/2002 | Peterson |

| | | | | | | |
|---|---|---|---|---|---|---|
| 6,409,651 B1 | 6/2002 | Brown, III | 7,083,566 B2 | 8/2006 | Tornes et al. |
| 6,409,943 B1 | 6/2002 | Lavie et al. | 7,179,912 B2 | 2/2007 | Halbrook et al. |
| 6,415,016 B1 | 7/2002 | Chornenky et al. | 7,182,726 B2 | 2/2007 | Williams et al. |
| 6,416,457 B1 | 7/2002 | Urick et al. | 7,194,063 B2 | 3/2007 | Dilmanian et al. |
| 6,419,621 B1 | 7/2002 | Sioshansi et al. | 7,208,748 B2 | 4/2007 | Sliski et al. |
| 6,421,416 B1 | 7/2002 | Sliski et al. | 7,220,225 B2 | 5/2007 | Dejuan, Jr. et al. |
| 6,422,989 B1 | 7/2002 | Hektner | 7,223,225 B2 | 5/2007 | DeJuan, Jr. et al. |
| 6,425,895 B1 | 7/2002 | Swanson et al. | 7,223,226 B2 | 5/2007 | Biscotti |
| 6,433,012 B1 | 8/2002 | Tuse et al. | 7,273,445 B2 | 9/2007 | Pulido et al. |
| 6,436,026 B1 | 8/2002 | Sioshansi et al. | 7,276,019 B2 | 10/2007 | DeJuan, Jr. et al. |
| 6,438,206 B1 | 8/2002 | Shinar et al. | 2001/0002427 A1 | 5/2001 | Verin et al. |
| 6,442,822 B1 | 9/2002 | Liprie | 2001/0009970 A1 | 7/2001 | Chornenky et al. |
| 6,443,881 B1 | 9/2002 | Finger | 2001/0016027 A1 | 8/2001 | Dinsmore |
| 6,443,976 B1 | 9/2002 | Flower et al. | 2001/0021382 A1 | 9/2001 | Ferrara et al. |
| 6,450,937 B1 | 9/2002 | Mercereau et al. | 2001/0027261 A1 | 10/2001 | Ciezki et al. |
| 6,450,938 B1 | 9/2002 | Miller | 2001/0036955 A1 | 11/2001 | Gerritsen et al. |
| 6,458,068 B1 | 10/2002 | Ellard et al. | 2001/0050971 A1 | 12/2001 | Feda et al. |
| 6,458,069 B1 | 10/2002 | Tam et al. | 2002/0015957 A1 | 2/2002 | Hageman et al. |
| 6,465,954 B1 | 10/2002 | Kerslick et al. | 2002/0021784 A1 | 2/2002 | Chornenky et al. |
| 6,471,630 B1 | 10/2002 | Sioshansi et al. | 2002/0040015 A1 | 4/2002 | Miller et al. |
| 6,471,636 B1 | 10/2002 | Sano et al. | 2002/0049247 A1 | 4/2002 | Chen |
| 6,473,491 B2 | 10/2002 | Chornenky et al. | 2002/0054664 A1 | 5/2002 | Tiren |
| 6,480,567 B1 | 11/2002 | Feda et al. | 2002/0054665 A1 | 5/2002 | Tiren |
| 6,482,142 B1 | 11/2002 | Winkler et al. | 2002/0055666 A1 | 5/2002 | Hunter et al. |
| 6,485,406 B1 | 11/2002 | Ziegler et al. | 2002/0065448 A1 | 5/2002 | Bradshaw et al. |
| 6,491,619 B1 | 12/2002 | Trauthen et al. | 2002/0072494 A1 | 6/2002 | Cao |
| 6,496,561 B1 | 12/2002 | Meyer et al. | 2002/0072645 A1 | 6/2002 | Chornenky et al. |
| 6,497,646 B1 | 12/2002 | Candelaria et al. | 2002/0090053 A1 | 7/2002 | Chornenky et al. |
| 6,497,647 B1 | 12/2002 | Tucker | 2002/0106055 A1 | 8/2002 | Cash |
| 6,506,145 B1 | 1/2003 | Bradshaw et al. | 2002/0107445 A1 | 8/2002 | Govari |
| 6,508,754 B1 | 1/2003 | Liprie et al. | 2002/0110220 A1 | 8/2002 | Shen et al. |
| 6,514,192 B2 | 2/2003 | Tiren | 2002/0115902 A1 | 8/2002 | Dejuan, Jr. et al. |
| 6,514,193 B2 | 2/2003 | Kaplan | 2002/0146090 A1 | 10/2002 | Chornenky et al. |
| 6,530,875 B1 | 3/2003 | Taylor et al. | 2002/0156003 A1 | 10/2002 | Lorens et al. |
| 6,546,077 B2 | 4/2003 | Chornenky et al. | 2002/0160954 A1 | 10/2002 | Hageman et al. |
| 6,551,291 B1 | 4/2003 | de Juan, Jr. et al. | 2002/0160979 A1 | 10/2002 | Banerjee et al. |
| 6,560,312 B2 | 5/2003 | Cash | 2002/0172829 A1 | 11/2002 | Mori et al. |
| 6,561,967 B2 | 5/2003 | Schmidt | 2002/0183253 A1 | 12/2002 | Brazzell et al. |
| 6,575,888 B2 | 6/2003 | Zamora et al. | 2002/0183302 A1 | 12/2002 | Strong et al. |
| 6,579,256 B2 | 6/2003 | Hughes | 2002/0193326 A1 | 12/2002 | Sukhatme |
| 6,582,417 B1 | 6/2003 | Ledesma et al. | 2003/0103973 A1 | 6/2003 | Rockwell et al. |
| 6,603,988 B2 | 8/2003 | Dowlatshahi | 2003/0144570 A1 | 7/2003 | Hunter et al. |
| 6,607,478 B2 | 8/2003 | Williams | 2003/0158480 A1 | 8/2003 | Tornes et al. |
| 6,623,418 B2 | 9/2003 | Smith | 2003/0179854 A1 | 9/2003 | Jaafar |
| 6,626,817 B2 | 9/2003 | Luth | 2003/0199726 A1 | 10/2003 | Gatto |
| 6,632,176 B2 | 10/2003 | McIntire et al. | 2003/0199848 A1 | 10/2003 | Ledesma et al. |
| 6,635,008 B1 | 10/2003 | Liprie | 2003/0204125 A1 | 10/2003 | Brauckman et al. |
| 6,638,205 B1 | 10/2003 | Chan et al. | 2003/0208096 A1 | 11/2003 | Tam et al. |
| 6,659,933 B2 | 12/2003 | Asano | 2004/0116767 A1 | 6/2004 | Lebovic et al. |
| 6,676,590 B1 | 1/2004 | Urick et al. | 2004/0199130 A1 | 10/2004 | Chornenky et al. |
| 6,676,607 B2 | 1/2004 | de Juan, Jr. et al. | 2004/0218721 A1 | 11/2004 | Chornenky et al. |
| 6,685,618 B2 | 2/2004 | Tam et al. | 2004/0218724 A1 | 11/2004 | Chornenky et al. |
| 6,689,043 B1 | 2/2004 | McIntire et al. | 2004/0225175 A1 | 11/2004 | Moody et al. |
| 6,692,481 B2 | 2/2004 | Guerrero | 2004/0245483 A1 | 12/2004 | Smit et al. |
| 6,692,759 B1 | 2/2004 | Wong et al. | 2005/0027156 A1 | 2/2005 | Pulido et al. |
| 6,709,381 B2 | 3/2004 | Munro, III | 2005/0031083 A1 | 2/2005 | Kindlein |
| 6,714,620 B2 | 3/2004 | Caflisch et al. | 2005/0049508 A1 | 3/2005 | Forman et al. |
| 6,719,750 B2 | 4/2004 | Varner et al. | 2005/0080340 A1 | 4/2005 | Stewart et al. |
| 6,749,553 B2 | 6/2004 | Brauckman et al. | 2005/0101825 A1 | 5/2005 | Winkler et al. |
| 6,755,776 B1 | 6/2004 | Granados | 2005/0124843 A1 | 6/2005 | Singh |
| 6,770,019 B1 | 8/2004 | Fritz et al. | 2005/0177019 A1 | 8/2005 | DeJuan, Jr. et al. |
| 6,771,737 B2 | 8/2004 | Kerslick et al. | 2005/0277802 A1 | 12/2005 | Larsen et al. |
| 6,786,905 B2 | 9/2004 | Swanson et al. | 2006/0025800 A1 | 2/2006 | Suresh |
| 6,799,075 B1 | 9/2004 | Chornenky et al. | 2006/0074303 A1* | 4/2006 | Chornenky et al. ......... 600/427 |
| 6,810,109 B2 | 10/2004 | Chornenky | 2006/0078087 A1 | 4/2006 | Forman et al. |
| 6,866,624 B2 | 3/2005 | Chornenky et al. | 2006/0084952 A1 | 4/2006 | Pallikaris et al. |
| 6,875,165 B2 | 4/2005 | de Juan, Jr. et al. | 2006/0100475 A1 | 5/2006 | White et al. |
| 6,914,960 B2 | 7/2005 | Swanson et al. | 2006/0111605 A1 | 5/2006 | Larsen et al. |
| 6,953,426 B2 | 10/2005 | Barber et al. | 2006/0142629 A1 | 6/2006 | DeJuan, Jr. et al. |
| 6,984,230 B2 | 1/2006 | Scheller et al. | 2006/0173479 A1 | 8/2006 | Smith |
| 7,018,371 B2 | 3/2006 | Forman | 2006/0189838 A1 | 8/2006 | Dejuan, Jr. et al. |
| 7,041,047 B2 | 5/2006 | Gellman et al. | 2006/0204535 A1 | 9/2006 | Johnson |
| 7,070,554 B2 | 7/2006 | White et al. | 2006/0217587 A1 | 9/2006 | DiCarlo et al. |

| | | | |
|---|---|---|---|
| 2007/0010746 A1 | 1/2007 | Forman et al. | |
| 2007/0016126 A1 | 1/2007 | Forman et al. | |
| 2007/0055089 A1 | 3/2007 | Larsen et al. | |
| 2007/0083129 A1 | 4/2007 | Mark | |
| 2007/0106108 A1 | 5/2007 | Hermann et al. | |
| 2007/0118010 A1 | 5/2007 | Hillstead et al. | |
| 2007/0123815 A1 | 5/2007 | Mark | |
| 2007/0142694 A1 | 6/2007 | Cutrer et al. | |
| 2007/0142695 A1 | 6/2007 | White et al. | |
| 2007/0166284 A1 | 7/2007 | Rasmussen et al. | |
| 2007/0167664 A1 | 7/2007 | Hermann et al. | |
| 2007/0167665 A1 | 7/2007 | Hermann et al. | |
| 2007/0265485 A1 | 11/2007 | DeJuan, Jr. et al. | |
| 2008/0275341 A1* | 11/2008 | Fehre et al. | 600/439 |

FOREIGN PATENT DOCUMENTS

| | | | |
|---|---|---|---|
| DE | 10 2005 056 080 A1 | 5/2007 | |
| EP | 0 541 699 B1 | 5/1996 | |
| EP | 0 778 788 B1 | 5/2003 | |
| EP | 1 060 765 B1 | 12/2004 | |
| EP | 1 317 945 B1 | 10/2005 | |
| EP | 1 369 143 B1 | 12/2005 | |
| EP | 1 060 764 B1 | 3/2006 | |
| EP | 0 993 843 B1 | 4/2006 | |
| EP | 1 529 554 B1 | 8/2006 | |
| GS | 1211316 | 11/1970 | |
| JP | 8131453 | 5/1996 | |
| JP | 2000350742 | 12/2000 | |
| WO | WO 98/01179 | 1/1998 | |
| WO | WO 00/33916 | 12/1998 | |
| WO | WO 99/42162 | 8/1999 | |
| WO | WO 01/43826 | 6/2001 | |
| WO | WO 2005/050393 A2 | 6/2005 | |
| WO | WO 2006/137831 A2 | 12/2006 | |
| WO | WO 2007/060051 A1 | 5/2007 | |

OTHER PUBLICATIONS

UIC Office of Technology and Management, "Intraocular Brachytherapy Device", 2003, (2 Pages) From: http://www.vpted.uillinois.edu/Events/iemerging/COAs/BrachytherapyCOA_2.pdf.

Finger et al , "Palladium 103 Opthalmic Plaque Radiotherapy", Arch Opthatmol-vol. 109 Nov. 1991 (pp. 1610-1613).

Finger at al , "Palladium 103 versus Iodine-125 for Opthalmic Plaque Radiotherapy" Int J Radiation Oncology Biol. Phys. vol. 27 (pp. 849-854), 1993.

Finger et al , "Opthalmic Plaque Radiotherapy for Age-related Macular Degeneration Associated with Subretinal Neovascularization" American Journal of Opthalmology, vol. 127, No. 2, 1999 (pp. 170-177).

Moore, R F., Choroidal sarcoma treated by the intraocular insertion of radon seeds, Apr. 1930, The British Journal of Opthalmology, vol. 14, pp. 145-152.

International Search Report for Application No. PCT/US 06/44335 dated Jan. 10, 2008.

Flaxel, Christina J. & Finger, Paul, "Age-Related Macular Degeneration", Marcel Dekker, Inc., (2002), ISBN: 0-8247-0682-X, pp. 224-234.

Flaxel, C.J. et al., "Radiation Treatment in Age-Related Macular Degeneration". Age-Related Macular Degeneration. Ed. Jennifer I. Lim. New York: Marcel Dekker, 2002. 225-238.

* cited by examiner

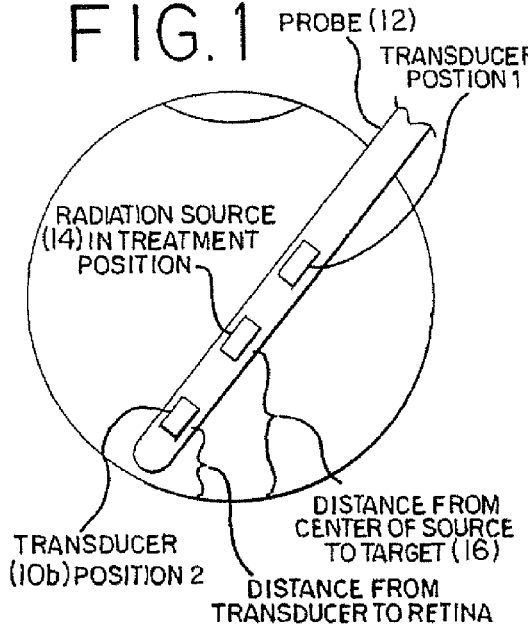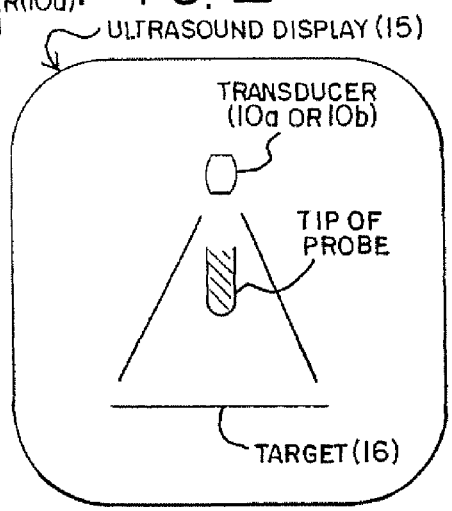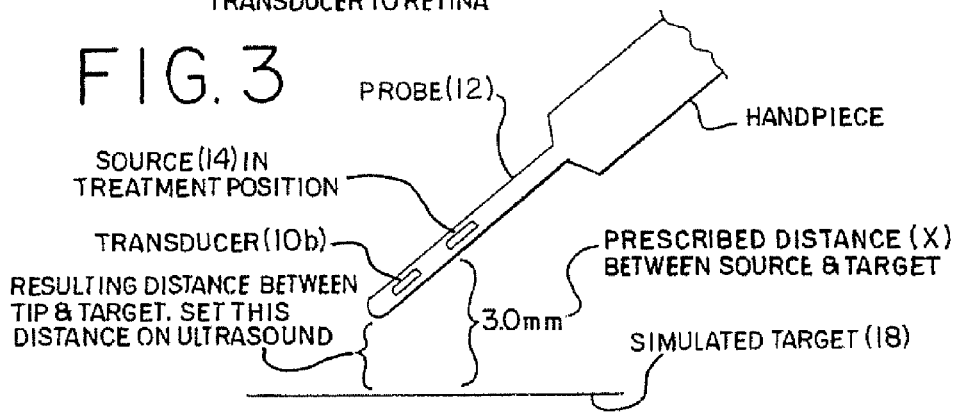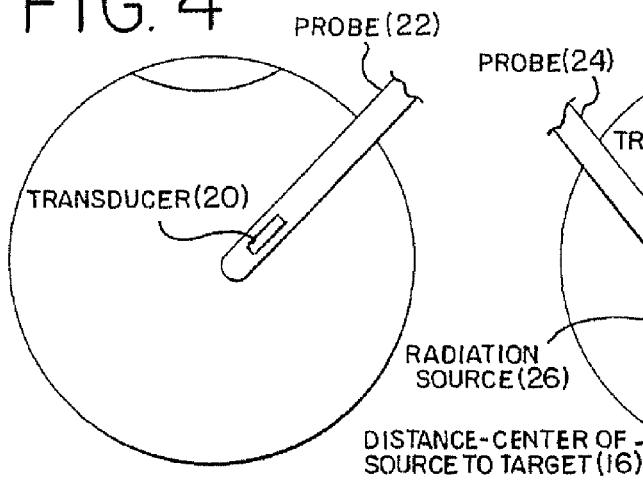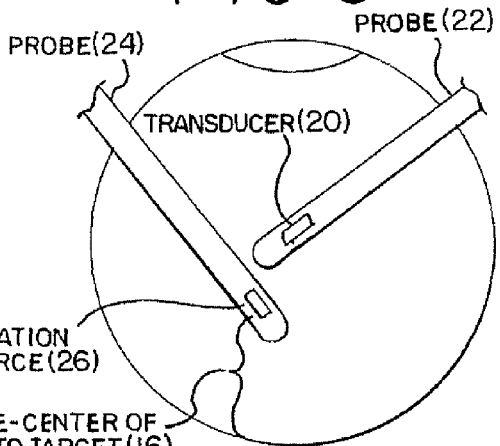

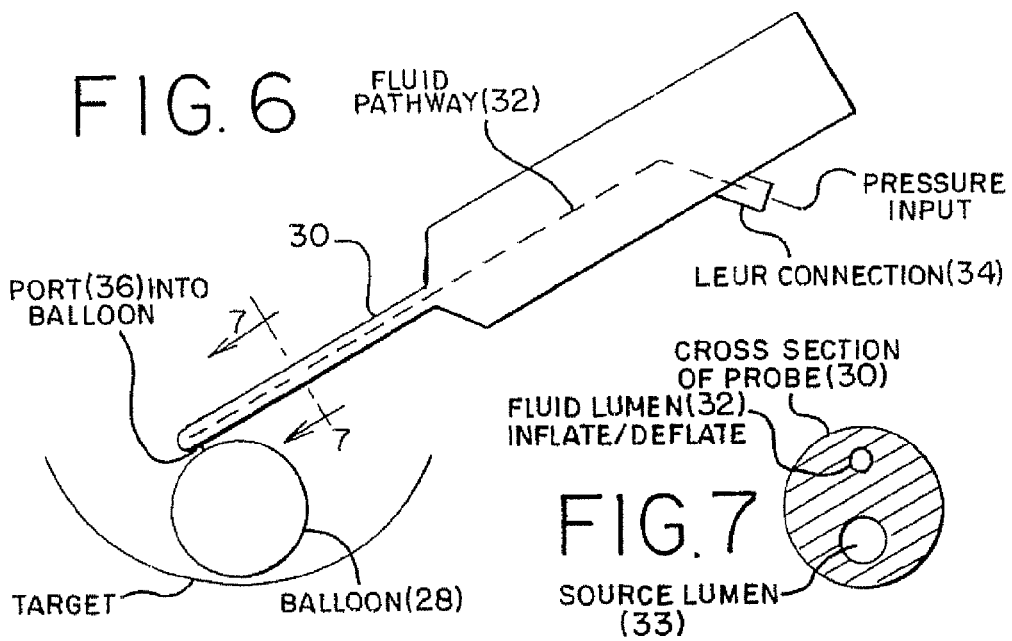
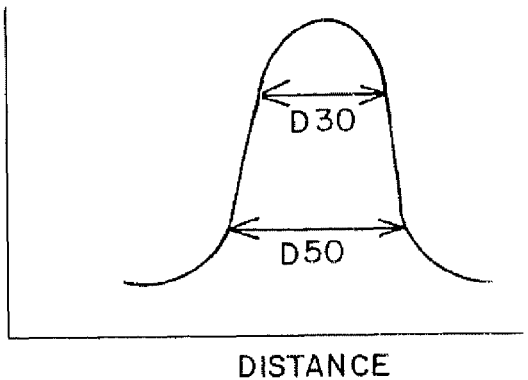
FIG. 8
DOSE
- LOWER INFLATION PRESSURE
- D30/D50 NARROW
- SHORT DWELL TIME
- HIGHER DOSE RATE
DISTANCE
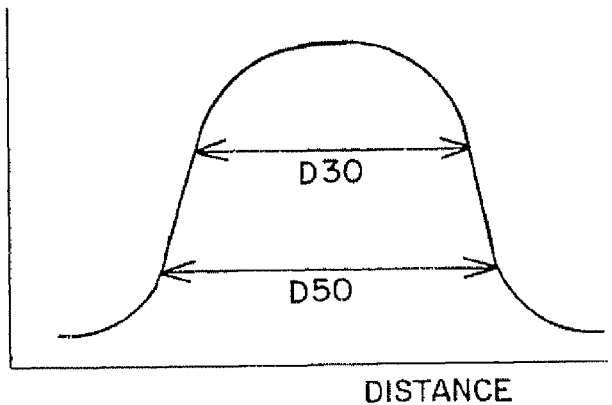
FIG. 9
DOSE
- HIGHER INFLATION PRESSURE
- D30/D50 BROAD
- LONGER DWELL TIME
- LOWER DOSE RATE
DISTANCE

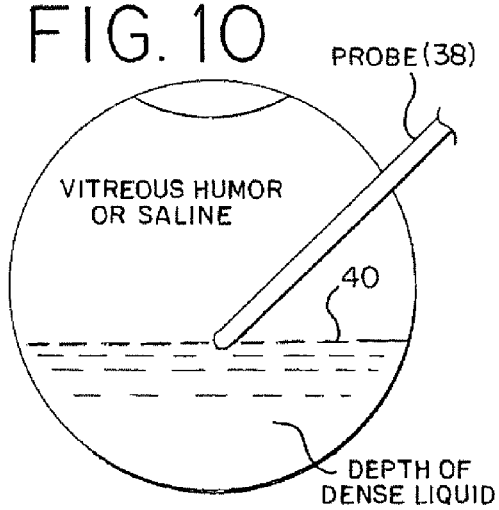
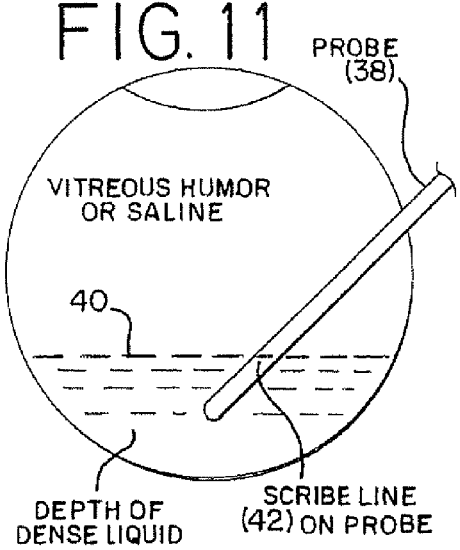
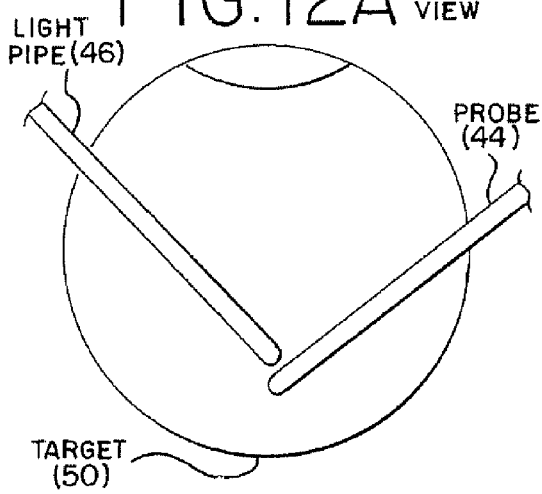
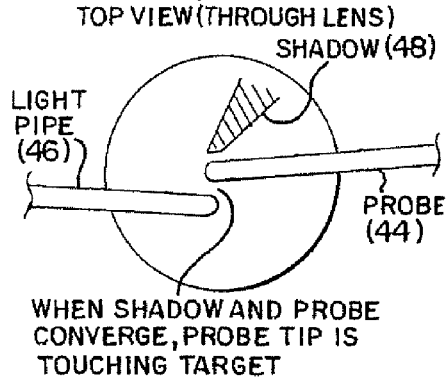
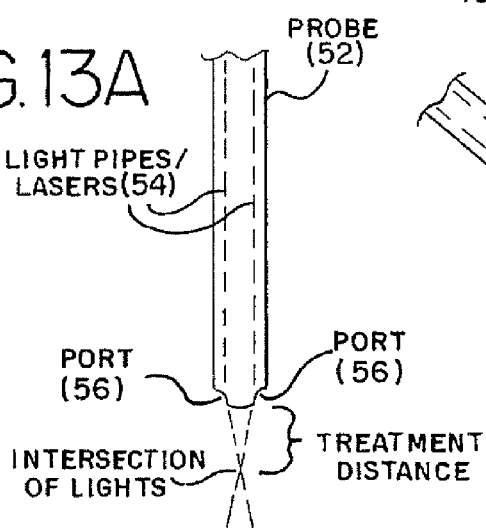
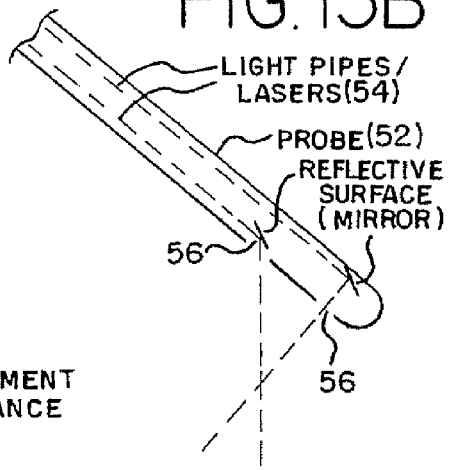

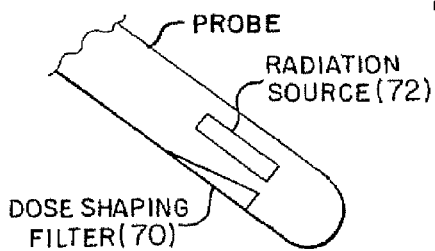
FIG. 16A
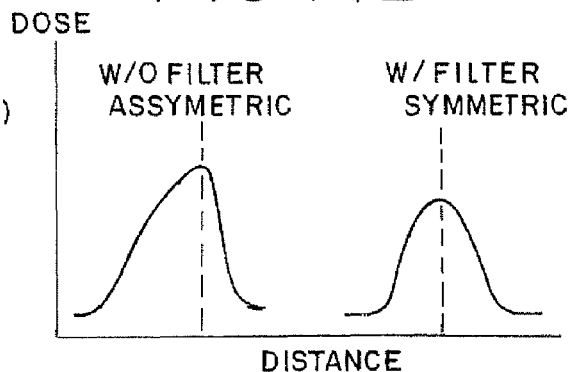
FIG. 16B
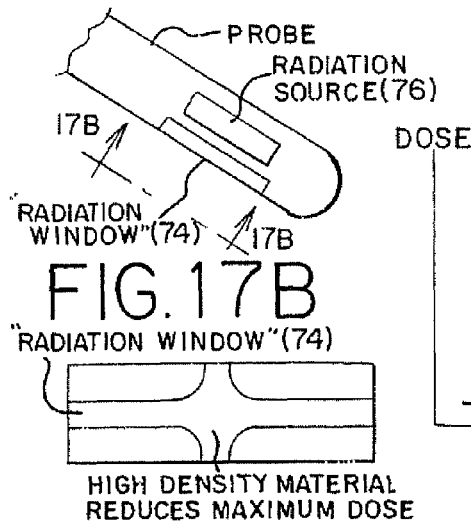
FIG. 17A
FIG. 17B
FIG. 17C
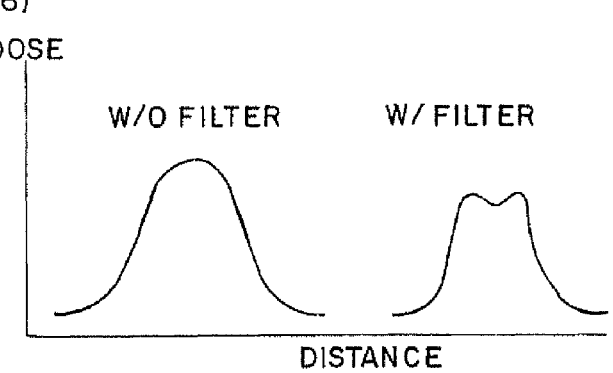
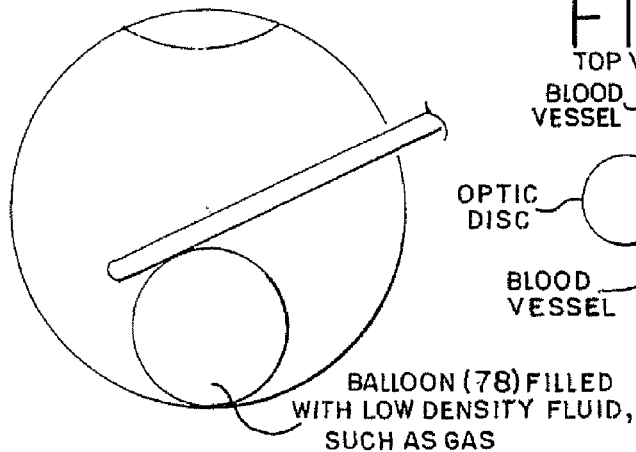
FIG. 18A
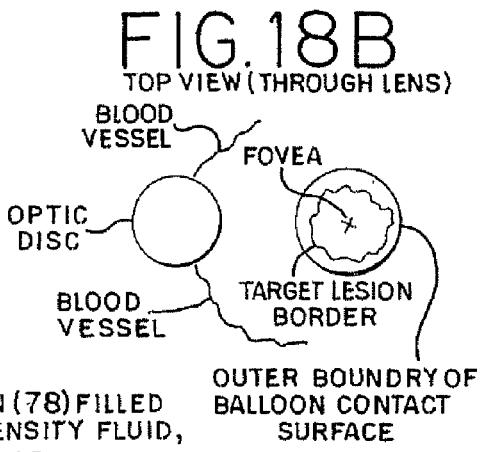
FIG. 18B

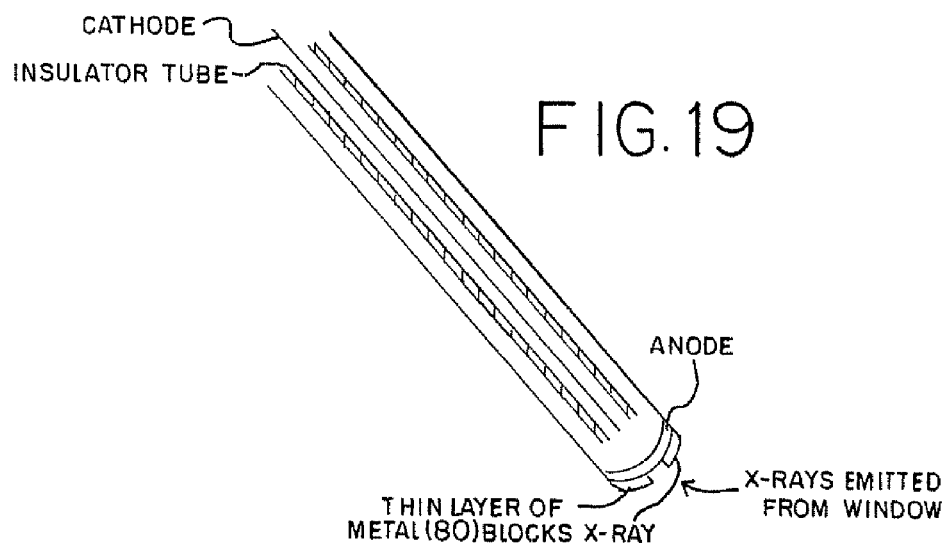
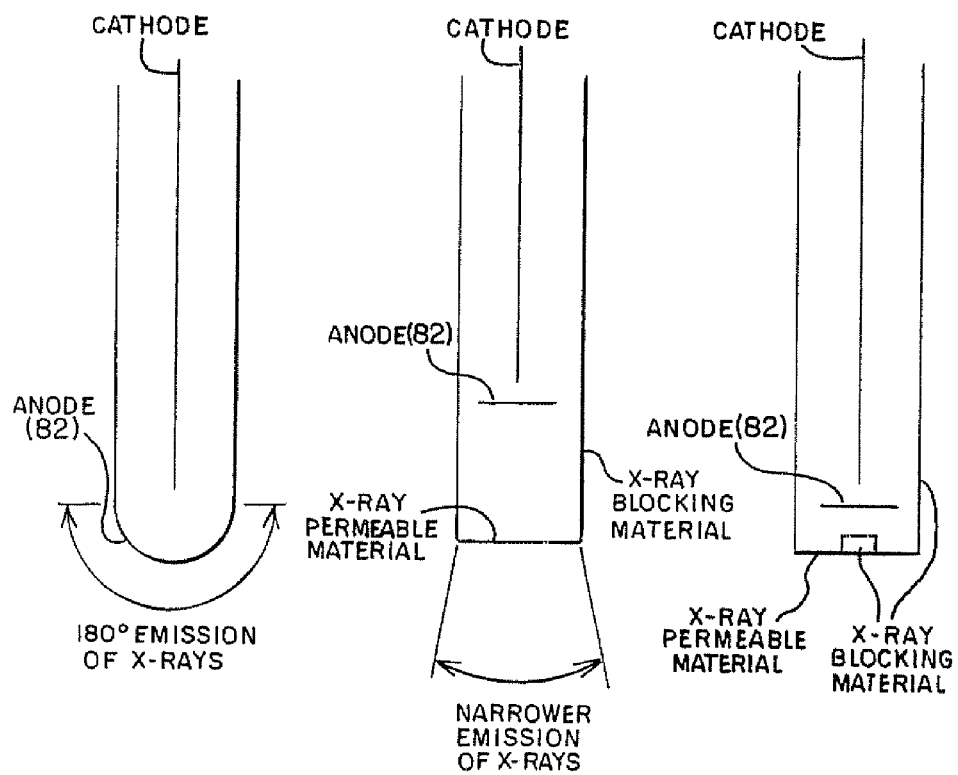

US 7,803,103 B2

METHODS AND APPARATUS FOR INTRAOCULAR BRACHYTHERAPY

CROSS REFERENCE TO RELATED APPLICATION

This application claims the benefit of U.S. Provisional Appln. Ser. No. 60/736,783 filed Nov. 15, 2005, and is a continuation in part of U.S. application Ser. No. 11/228,030, filed Sep. 15, 2005, now U.S. Pat. No. 7,563,222 which is a continuation in part of U.S. application Ser. No. 11/056,763, filed Feb. 11, 2005 now U.S. Pat. No. 7,744,520 and claims the benefit of U.S. Prov. Appln. Ser. No. 60/554,001, filed Feb. 12, 2004, all of which are incorporated herein by reference.

BACKGROUND OF THE INVENTION

It has been proposed to treat age-related macular degeneration (AMD) by irradiating the choroidal neovascularization (CNV) underlying the retina that is associated with AMD with ionizing radiation (such as beta or x-ray radiation). See, generally, U.S. Pat. No. 6,875,165 and U.S. Pub. Appln. No. 2003/0179854, both of which are incorporated herein by reference. Certain apparatus for the intraocular delivery of radiation, either epi-retinally or sub-retinally, and methods of their use are disclosed in the co-pending U.S. application Ser. No. 11/056,763, filed Feb. 11, 2005 and Ser. No. 11/228,030, filed Sep. 15, 2005, identified above.

As noted in the above-referenced patents and applications, Beta radiation, and some forms of x-ray radiation, are advantageous for treating AMD because the dose delivered by such radiation sources decays roughly with the square of distance in materials with similar density to water (such as human tissue). Therefore, by accurately positioning the radiation source or emitter in close proximity to the target tissue (in this case the CNV, and/or taking steps to avoid irradiating non-target tissue by, e.g. the use of masks or attenuating substances and filters, a therapeutic radiation dose can be delivered to the target tissue, while delivering little or no dose to non-target tissues (such as surrounding ocular or non-ocular structures). The present application discloses a variety of methods and apparatus for accomplishing such accurate targeting of treatment.

SUMMARY OF THE INVENTION

In one aspect of the invention, a device for local, directional intraocular delivery of radiation to a target tissue is provided. The device includes a cannula sized for insertion into an eye and having a proximal end and a distal end. A radiation-emitting source is adapted to be located in the distal end of the cannula, and an ultrasound transducer is also located in the distal end of the cannula. In one embodiment, the ultrasound transducer is located proximal to the radiation-emitting source, while in a second embodiment, the ultrasound transducer is located in the cannula distal to the radiation-emitting source.

In another aspect of the invention, a method for positioning a device including an ultrasound transducer as described above is provided. The method includes calibrating the ultrasound transducer in accordance with a predetermined spacing for the distal end of the cannula relative to the target tissue so as to generate a signal when the predetermined spacing is achieved. The cannula is then introduced into the interior of the eye through an access site in the surface of the eye and the distal end of the cannula is moved toward the target tissue until the signal generated by the ultrasound transducer is perceived by the user. In one aspect of the method, the signal generated by the ultrasound transducer is an audible signal, while in another aspect of the invention, the signal is a visual signal.

In another aspect of the invention, a method for positioning a first cannula having a radiation emitter in the interior of an eye by means of a second cannula with an ultrasound transducer is provided. First, the first cannula is introduced into the interior of the eye through an access site in the surface of the eye. Then, the second cannula is introduced into the interior of the eye through an access site in the surface of the eye. Then, the distal end of the first cannula is positioned between the ultrasound transducer associated with the second cannula and the target tissue. Then, the distal portion of the first cannula is moved toward the target tissue until a predetermined spacing between the distal end of the first cannula and the target tissue is achieved, at which time a signal is generated by the ultrasound transducer. Again, the signal may be either an audible signal or a visual signal.

In another aspect of the invention, a method for positioning a cannula for intraocular delivery of a therapeutic treatment to a target tissue on the interior of an eye is provided. First, a cannula is provided having an inflatable balloon that obtains a predetermined size when inflated to a predetermined pressure, the predetermined size corresponding to a desired spacing between the cannula and the target tissue for the delivery of the therapeutic treatment. The balloon may be either compliant or non-compliant. The cannula is introduced into the interior of the eye through an access site in the surface of the eye and the balloon is inflated to the predetermined pressure. Then, the cannula is advanced toward the target tissue until the target tissue is contacted by the inflated balloon. The balloon is preferably inflated with a fluid having a density lower than the density of the fluid displaced by the inflation of the balloon, thus resulting in a reduced treatment time. In another aspect, the balloon is selected to have a shape corresponding to the shape of the target tissue.

In another aspect of the invention, a method for positioning a cannula on the interior of an eye is provided in which the fluid in the interior of the eye is displaced with a known volume of a second fluid having a density different from the density of the first fluid so as to create a visual interface between the first fluid and the second fluid that is spaced a predetermined distance from the target tissue. The cannula is then introduced into the interior eye through an access site in the surface of the eye and advanced toward the interface of the first fluid and the second fluid until the distal end of the cannula contacts the interface. The cannula may optionally be provided with visible mark proximal to the distal, in which case the distal end of the cannula is advanced through the interface of the first fluid and the second fluid until the visible mark on the cannula is aligned with the interface. The second fluid may have a density either greater than or less than the density of the first fluid.

In another method according to the present invention, a method is provided for positioning a first cannula for treatment of target tissue on the interior of an eye in which the distal end of the cannula is in contact with the target tissue. A second cannula is introduced into the interior of the eye through an access site in the surface of the eye, the second cannula having a light source that projects a beam of light toward the target tissue. The first cannula is introduced into the interior of the eye through a second access site on the surface of the eye so that the distal end of the first cannula is between the second cannula and the target tissue so as to be within the beam of light projected toward the target tissue by the second cannula. This casts a shadow by the distal end of the first cannula that falls on the target tissue, with the shadow being observable through the lens of the eye. The distal end of the first cannula is then advanced toward the target tissue until the tip and the shadow cast by the tip coincide, thus indicating contact of the distal end of the first cannula with the target tissue.

In another aspect of the invention, device is provided for local, directional intraocular delivery of a therapeutic treatment to a target tissue that comprises a cannula, a therapeutic treatment source adapted to be located in the distal end of the cannula that is intended to be spaced a predetermined distance from the target tissue, and at least one source of light adapted to project two visible beams of light out the distal end of the cannula. The two beams of light form an intersection such that when the intersection is coincident with the target tissue, the treatment source is spaced the predetermined distance from the target tissue. The source of light preferably may either be a light pipe or a laser.

In another aspect of the invention, a device for local intraocular delivery of therapeutic treatment of a target tissue is provided that has a reduced surface friction. This reduced surface friction may be achieved by electro polishing the surface of the cannula, dimpling the surface of the cannula, applying a liquid lubricant, such as glycerin, to the surface of the cannula, or providing the surface of the cannula with a radiation-resistant, low-friction coating.

In another aspect of the invention, a method for delivering x-ray radiation to a target tissue in an eye from the interior of the eye is provided in which an x-ray probe with an x-ray emitter associated therewith is introduced into the interior of the eye through an access site in the surface of the eye. The probe is positioned with respect to the target tissue, and the x-ray emitter is intermittently activated until a desired radiation dose is delivered to the target tissue. The x-ray emitter may be activated and de-activated by a thermocouple located in the interior of the eye which is preferably associated with the probe. The x-ray probe may also have a heat exchanger associated therewith that includes flow path for receiving a cooled fluid. In addition, the heat exchanger may comprise a sheath that is preferably made of a material having a low coefficient of thermo conductivity.

In another aspect of the invention, a device for local, directional intraocular delivery of radiation to a target tissue is provided that comprises a probe sized for insertion into the eye with a radiation-emitting source having a predetermined length adapted to be located in the distal end of the probe. A filter is associated with the distal end of the probe that blocks a greater amount of radiation at the distal end of the radiation-emitting source than at the proximal end, resulting in a generally symmetrical dose profile delivered to the target tissue when the probe is oriented at an angle with respect to target tissue. In one embodiment, the filter is greater in thickness adjacent the distal end of the radiation-emitting source than adjacent the proximal end. Alternatively, the filter may have a higher density adjacent the distal end of the radiation-emitting source than adjacent the proximal end.

In another aspect of the invention, a device for local, directional intraocular delivery of x-ray radiation is provided in which a layer of high density metal is associated with the distal end of the cannula in proximity to the anode for attenuating x-ray radiation. The metal layer has an opening therein to allow x-ray radiation to pass therethrough substantially unimpeded, the opening being located in size to direct and confine the x-ray radiation to the target tissue.

In another aspect of the invention, a device for local, directional intraocular delivery of x-ray radiation is provided in which the distal end of the cannula and the anode have a hemispherical shape. Alternatively, the distal end of the cannula and the anode can be generally planar and oriented generally perpendicular to the longitudinal axis of the distal end of the cannula.

In another aspect of the invention, a method for treating target tissue on the interior of the eye with both radiation and an anti-VEGF pharmaceutical is provided. The administration of the two different types of therapies occurs within a period of time of fourteen days or less, and is preferably performed in a period of time of four hours or less, even more preferably during the same procedure. The pharmaceutical may be administered either prior to or subsequent to the irradiation of the target tissue. Follow-up doses of the pharmaceutical may be given, preferably two to eight weeks after the first treatment.

BRIEF DESCRIPTION OF THE FIGURES OF THE DRAWINGS

FIG. 1 is a schematic representation of an ultrasound technique for positioning a treatment probe with respect to a target tissue in the interior of the eye.

FIG. 2 is a schematic representation of a visual display for an ultrasound positioning technique as described in connection with FIG. 1.

FIG. 3 is a schematic representation of a method for calibrating an ultrasound positioning system as described in connection with FIG. 1.

FIGS. 4 and 5 are schematic representations of a method for positioning a treatment probe in the interior of the eye in which the ultrasound transducer is mounted in a separate probe from the probe containing the radiation emitter.

FIG. 6 is a schematic representation of a treatment probe having a spacing balloon secured thereto at its distal end.

FIG. 7 is a cross-sectional view of the probe of FIG. 6.

FIGS. 8 and 9 are graphic representations of the dose administered versus distance from the radiation source showing the contrast in dose distribution between spacing of radiation source achieved by a small balloon (FIG. 8) and the dose distribution when a relatively larger balloon is used (FIG. 9).

FIGS. 10 and 11 illustrate a method for positioning a probe on the interior of an eye in which a fluid is injected into the eye that has a density different (higher) from that of the fluid inside the eye.

FIGS. 12A and 12B schematically illustrate a method for positioning a delivery probe on the interior of the eye using a separate light source.

FIGS. 13A and 13B schematically show two alternatives for positioning a probe in which the probe has a pair of light sources integral therewith.

FIGS. 16A-B and 17A-C schematically illustrate radiation delivery probes including means for shaping the radiation dose field (FIG. 16A, 17A, 17B) and the effect that the incorporation of such means has on the dose field (FIGS. 16B, 17C).

FIGS. 18A and 18B schematically illustrate a method for protecting non-target tissue in which a balloon is affixed to the delivery probe.

FIGS. 19 and 20A-C show means for shaping the dose profile of an x-ray radiation probe.

DETAILED DESCRIPTION OF THE DISCLOSED EMBODIMENTS

Figure 14:
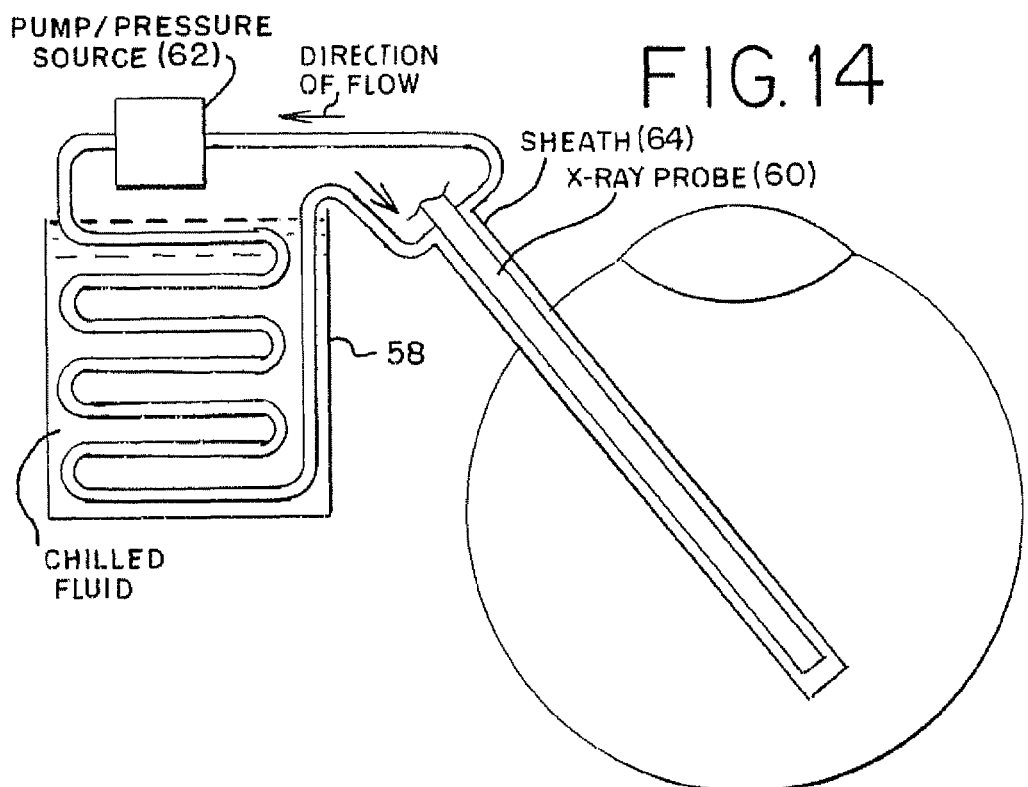
FIG. 14 schematically shows an x-ray radiation probe having a heat exchanger associated therewith.

Various methods and apparatus for targeted delivery of a radiation dose are described in detail below.

Positioning the Radiation Source

One way of properly spacing the radiation source from the target tissue is to use various distance feedback systems that are generally known in the art. For example, an RF ("radio-frequency") or Ultrasound transmitter can be attached to radiation delivery probe/cannula disclosed in the above-referenced patents and applications. Specifically, with reference to FIG. 1, an ultrasound transducer 10a or 10b can be mounted in the probe 12 either proximal to the radiation emitter 14, "transducer position 1 (for transducer 10a), or distal to the radiation emitter 14, "transducer position 2" (for transducer 10b). The transducer generates and senses ultrasound energy. The transducer is activated by an externally actuated switch so that, when turned on, the transducer alternately generates pulses of ultrasound energy and listens for feedback signals. The feedback is then converted to a visual display 15, as shown in FIG. 2, or an audible signal to the user, thus providing distance information about the location of the probe with respect to the target tissue 16. The preferred position of the ultrasound transducer is distal to the radiation source or emitter 14 (i.e., transducer 10b). If the transducer is distal to the radiation source or emitter, the transducer can be relatively larger, as the radiation source 14 does not have to pass through or around the transducer when being moved to the treatment position.

The transducer may emit ultrasound waves either toward the target tissue or toward the tip of the probe. If the prescribed dose is calculated assuming a space between the probe tip and the retina, the transducer is directed so as to emit ultrasound toward the target tissue, and calibration is required prior to treatment. Ultrasound distance calibration techniques are well known in the art, and will not be discussed in detail. As an example, and as schematically illustrated in FIG. 3, assuming that the optimal distance "X" between the center of the radiation emitting source 15 and the target tissue is 3.0 mm, during calibration, the actual separation between the transducer 10b and the tissue 16 in order to achieve a 3.0 mm tissue to source separation is determined outside the eye by using a target 18, typically a plastic material, that has a density comparable to the vitreous humor, saline (post vitrectomy) or the target tissue, which is essentially the density of water. To calibrate, the probe 12 is loaded into a fixture and the transducer 10b is turned on. The system's software is used to identify the current position as the "treatment position." Calibration may be done either at the place of manufacture of the device or at the clinical site. An ultrasound display, such as shown in FIG. 2, preferably viewable through the eyepiece of the surgical microscope, would permit the surgeon to visualize the ultrasound output to determine when the probe is properly positioned. Alternatively, or additionally, an audible signal can be provided when the desired spacing is reached, as described in greater detail below.

In certain circumstances, the transducer may emit ultrasound toward the tip of the probe, for example, when the radiation source is to be positioned by touching the probe against the surface of the target tissue. In such cases, calibration is optional. If the prescribed dose is calculated assuming contact between the probe tip and the retina, the surgeon can visualize the ultrasound output directly through the eyepiece and determine when contact is made. If the prescribed dose is calculated assuming some separation between the probe tip and the retina, the system will have to be calibrated either after manufacture or prior to treatment as described above. If the ultrasound is directed toward the tip, the tip may be made from a material with a lower density than the metal from which the probe is constructed, such as silicone or a fluid-filled balloon. This should prevent a shadow from the high density metal appearing in the ultrasound images, and is more atraumatic to the tissue.

In a further option (as shown in FIG. 4), the ultrasound transducer 20 may be part of an instrument 22 that is entirely separate from the radiation delivery probe. In this case, the ultrasound transducer 20 is either introduced into a separate opening within the eye where it is positioned in the vitreous cavity, or it is positioned external to the eye. The radiation probe 24 having emitter 26 is located between the ultrasound transducer and the target tissue 16, as shown in FIG. 5.

In each instance, the output from the transducer provides the surgeon with real time position feedback so that the surgeon can adjust the position of the probe to ensure the prescribed dose of radiation is delivered. For example, a discrete tone or beep can be generated at one-second increments when the probe is distant from the target. The beep frequency increases as the probe gets closer to the target. If the probe comes in contact with the target, the beep tone sounds continuously. While the radiation exposure of the target tissue is occurring, a recording device collects data that describes the location of the probe over the duration of the treatment. This data may be used for post-procedure analysis of the dose delivered. The output may be analyzed to determine both the position of the source and the length of time it was in each position. When this information is combined with the dose rate of the radiation source, a precise dose delivered to the target tissue can be calculated.

Alternatively, the radiation source may be appropriately spaced from the target tissue through the use of a compliant balloon that forms a part of the delivery probe. Specifically, as illustrated in FIG. 6, a balloon 28 made from a compliant or semi-compliant, material such as latex or silicone, is attached to the distal tip of the radiation delivery probe 30. The balloon 28 is designed with specific pressure/size relationship. With reference to FIG. 7, the probe is provided with a lumen 32 (in addition to the radiation source lumen 33) for inflating the balloon 28. The proximal end of the inflation lumen 32 terminates outside the eye with a luer connection 34, while the distal end of the inflation lumen 32 terminates at the distal end of the probe 30 underneath the balloon 28 with a hole or port 36 for the fluid to escape to inflate the balloon. A pressure source such as a pump or inflation syringe filled with an inflation fluid (gas or liquid) is attached to the proximal luer connection 34. The pressure source includes means to monitor the pressure of the closed system. The fluid for inflating the balloon may be compressible (such as nitrogen, air, carbon dioxide) or incompressible (such as saline, glycerin, or oil). The pressure source is activated and the fluid inflates the balloon to the desired pressure. The balloon is designed so that lower pressures correlate to known smaller volumes, while higher pressures correlate to known larger volumes for the balloon. The balloon is inflated to the pressure desired to position the radiation source the desired distance from the tissue. When the balloon is inflated to the desired pressure, the probe/inflated balloon is moved toward the retina so that the radiation source is positioned over the target tissue and the balloon is in light contact with the retina. After the radiation is delivered, the balloon is deflated and the system withdrawn from the eye.

The farther the radiation source is positioned from the tissue, the broader the treatment field and the longer the source must remain in position to achieve the prescribed dose. This phenomenon is illustrated in FIGS. 8 and 9. Consequently, one advantage of using a low density fluid (e.g., a gas) to inflate the balloon is that the radiation is not significantly attenuated by the gas, and the radiation source thus delivers a higher dose rate per unit time than if the balloon is filled with a high density material. Additionally, the dose distribution will be spatially more uniform with a low density fluid. The balloon geometry may be spherical, cylindrical, cubic, pyramidal, etc. depending upon the desired performance characteristics. The balloon has the additional benefit of creating a relatively soft contact with the retina when compared with touching the retina directly with the metal probe. Additionally, the load originating from the surgeon's hand and being transmitted to the retina via the radiation delivery probe is distributed over a much larger surface area when the balloon is used to contact the retina.

As an alternative to the use of a compliant balloon, a non-compliant balloon made from a material such as PET may be attached to the distal tip of the radiation delivery probe. The non-compliant balloon is inflated to a pre-determined pressure with any of the fluids described above so as to be inflated to a known volume which cannot be adjusted. The known volume positions the probe a known distance from the target tissue. The procedure is the same as set forth above with respect to the use of a compliant balloon.

With reference to FIGS. 10 and 11, a further alternative method for properly positioning the treatment probe 28 with respect to the target tissue involves creating a "bubble" in the interior of the eye by injecting a known volume of fluid having either a higher density than saline or vitreous humor into the eye, or a lower density than saline or vitreous humor, such as a gas. The volume of fluid to be injected is calculated assuming a common eye geometry or after measuring the patient's eye and is based upon the desired depth of the fluid. The depth of the fluid determines the interface 40 between the vitreous fluid or saline and the newly introduced fluid. This depth is used as a signal for the surgeon when positioning the tip of the device. Through the microscope, the surgeon can see when the tip of the device 38 touches the higher density fluid, as shown in FIG. 10. This is an indication to the surgeon that the appropriate distance of separation between the tip of the device 38 and the target tissue has been reached and that the radiation dose can be delivered. During treatment, the surgeon maintains the tip in this exact position. Alternatively, if the tip of the probe 38 is to be located at a position interior of the interface 40 between the low and high density fluids, the external surface of the probe 38 may include a scribe line 42 or other visual marking indicating the extent to which the probe 38 is to be advanced beyond the interface 40. Under microscopic visualization, the surgeon can then align this visual indicator with the fluid interface and deliver the source, as shown in FIG. 11. After treatment, this dense fluid may be removed and replaced with saline using standard vitrectomy techniques.

A further technique for positioning the tip of the probe in gentle contact with the target tissue, illustrated in FIGS. 12A-B, involves the creation of a shadow from the probe 44 on the interior of the eye that can be visualized through the patient's lens by the surgeon during vitreoretinal surgery through the microscope. To this end, the surgeon may use a standard endoilluminator or light pipe 46 in conjunction with the probe tip. When the light pipe 46 is correctly positioned with respect to the probe, it casts a shadow 48 from the probe onto the retinal surface 50. By visualizing the shape and position of the shadow 48, the surgeon can determine the position of the probe tip with respect to the retina 50. As the surgeon moves the probe 44 toward the retina 50, the tip of the shadow 48 and the probe 44 converge and eventually overlap, thus signaling contact with the retina 50. When the surgeon moves the probe 44 away from the retina 50, the tip of the shadow 48 and the probe 44 move farther apart.

In a further method for positioning the probe, illustrated in FIGS. 13A, 13B, the probe 52 is provided with one or two light pipes or lasers 54 and two ports 56 at the distal end of the probe 52 to allow the light sources 54 to escape the probe 52. The lights 54 are focused in a way such that they intersect at a predetermined distance away from the probe 52 corresponding to the distance the probe 52 is to be spaced above the target tissue so that the source is positioned at the desired height above the target tissue. The surgeon turns on the light(s) 54, moves the probe 52 toward the retina and when the intersection of the two beams reaches the target tissue, the probe 52 is the desired distance away from the target tissue.

Reduction of Traction Between the Probe and the Vitreous Humor

Vitreoretinal surgery requires instruments designed for the unique environment of the eye that are also compatible with existing surgical instruments. The probe of the radiation delivery device used in the present invention preferably has a cross-section compatible with existing 20 gauge surgical instruments, including trocars. Probes sized larger than 20 gauge increase the likelihood for complications, such as retinal detachments, due to traction. This is due to the increased surface area of the probe and the volume displacement of the probe as it is inserted into the eye. To decrease the traction between the probe and the vitreous humor, the outer surface of the probe, if made of metal, can be electropolished to provide a smooth surface, thereby reducing the surface friction. Alternatively, the surface of the probe may be dimpled (similar to a golf ball) on either a micro or macro level using known surface finishing or machining techniques. The dimpling of the outer surface of the probe reduces surface friction under flow conditions (such as insertion and removal of the probe).

Additionally, a liquid lubricant, such as glycerin or Hinge Free instrument lubricant (available from Steris Corporation), can be applied to the outer surface of the probe to further reduce the friction at the probe/vitreous humor interface. Further, the probe can be provided with a low friction coating to achieve the same goal.

Heat Regulation with X-Ray Emitters

The generation of x-rays within the eye could elevate the temperature inside the eye above the threshold for tissue damage. To limit the heat transmitted to the eye, several strategies could be employed. First, rather than being continuously on, the x-ray generator can be pulsed, with it automatically alternating between on and off at a known frequency. Additionally, the frequency of the pulsing can be regulated by a thermocouple inside the eye (either incorporated into the x-ray probe or inserted via a different port). Additionally, or alternatively, means for cooling the emitter can be employed. For example, with reference to FIG. 14, a heat exchanger 58 may be incorporated external to the electrodes of the x-ray probe 60, and a cooled fluid (gas or liquid) is circulated through the heat exchanger by means of a pump or other pressure source 62 to reduce the overall heat load of the x-ray probe 60. In addition, the x-ray emitter 60 can be provided with a sheath 64 between the heat source (electrodes) and the eye made from a material with a low coefficient of thermal conductivity.

Figure 15:
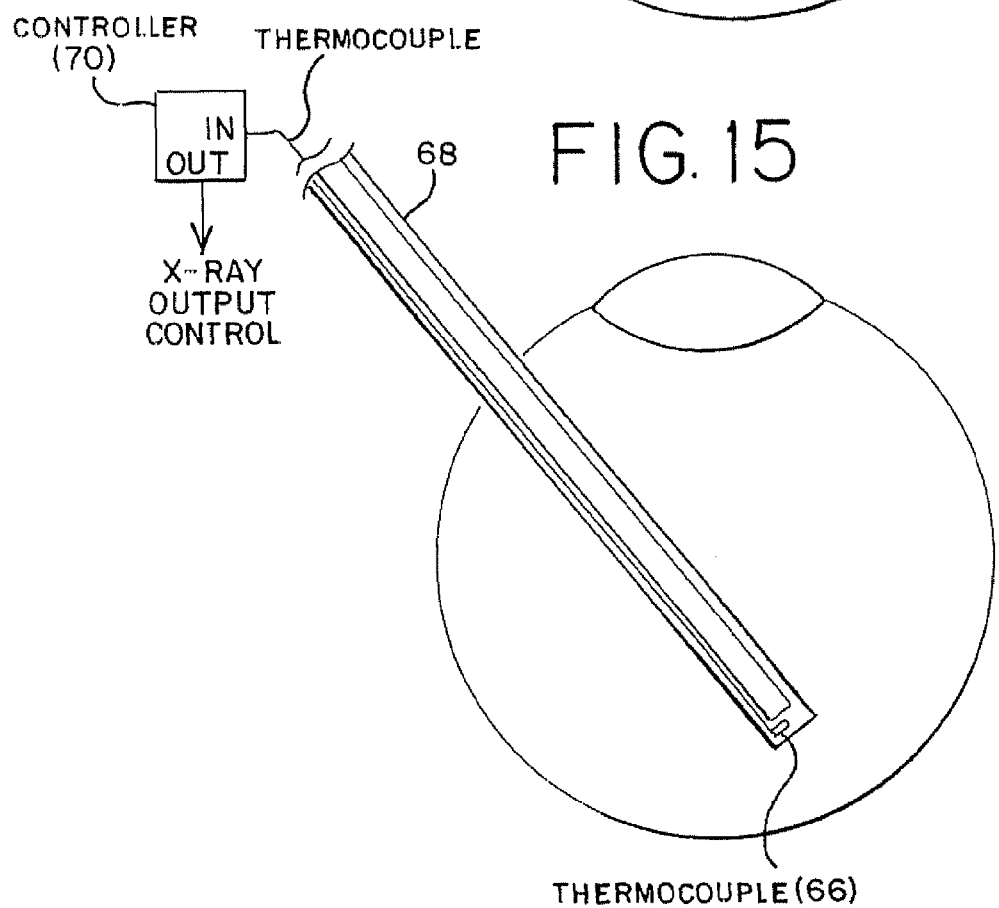
FIG. 15 schematically illustrates an x-ray radiation probe that includes thermocouples for proving temperature data.

In addition, as shown in FIG. 15, a thermocouple 66 or other temperature sensing instrument can be placed at or near the anode of the x-ray probe 68 to provide temperature data feedback to the x-ray controller 70. When the temperature has exceeded certain thresholds, the controller 70 may automatically adjust the energy output of the x-ray system.

Dose Distribution and Protection of Non-Target Tissue

Beta radiation and low energy x-ray radiation each have a rapid dose fall-off when traveling through water as compared to forms of gamma radiation. Other forms of external radiation can control the depth of penetration within a few centimeters; however, the dose distribution is less controlled than beta and low energy x-ray radiation. The probe of the present invention has the advantage of providing precise control over the dose distribution and depth of penetration over other radiation alternatives.

The use of a "targeted" radiation approach, with the masking of non-target tissue and/or attenuation of radiation other than that directed to the target tissue with filters and the like, allows a higher total dose delivered to the target tissue while lowering the risk of collateral damage to the surrounding ocular structures. When a targeted approach is not employed (such as with alpha or gamma radiation sources), the total dose is limited due to the risk to nearby ocular structures. Additionally, the risk for radiation retinopathy is lowered when a smaller volume of tissue is irradiated, and the healing response of the irradiated tissue is improved with a targeted approach.

Protecting the healthy areas of the retina is desirable because it lowers the risk of radiation-induced side effects. The dose distribution may be masked by placing a shaping filter 70 behind the radiation source 72 (as shown in FIG. 16A), by creating a radiation window 74 between the source 76 and the tissue (as shown in FIGS. 17A, 17B), or by introducing low density fluid between the radiation source and the tissue (such as the use of a gas for the inflation fluid for the spacing balloons discussed above and shown in FIG. 6). The shaping filter 70 and radiation window 74 are made from a high density material, such as platinum iridium, and serve to shape the dose distribution such as making the distribution more uniform, widening the distribution and/or narrowing the distribution, as shown schematically in FIGS. 16B and 17C. See, e.g., WO 2005/049139, which is incorporated herein by reference. The radiation window 74 could create similar modifications to the dose distribution. Generally, adding a shaping filter 70 or radiation window 74 serves to increase the overall dwell time.

Because of the roughly hemispherical shape of the retina and the many angles of entry for the radiation probe, it may be desirable to have the ability to direct the radiation out of the probe. Beta radiation is blocked by thick and/or dense material. By using dense material, the emission of Bremstrahlung (secondary gamma radiation) is increased. By altering the density and/or thickness of the metals at the tip of the device, the shape of the beta dose field may be altered, as shown in FIG. 16B.

Alternatively, with reference to FIGS. 18A and 18S, a balloon 78 filled with a lower density fluid than saline (such as gas) could be placed between the source and the tissue. The low density fluid would not attenuate the radiation as much as the surrounding vitreous humor or saline. This would result in reduced treatment times when compared to delivering the therapy through the vitreous humor. The shorter treatment times result in greater protection for other ocular structures that are masked by the comparably high density saline or vitreous humor. The balloon would be shaped to correspond to the shape of the target tissue so that the tissue in contact with the balloon would be treated while tissue outside the contact area with the balloon would be masked. Numerous balloon geometries could be envisioned to match the shape of the lesion. Shaping the balloon so that the contact area corresponds to the lesion shape also reduces the likelihood of ischemia in the target tissue. The procedural steps and basic probe design are disclosed above.

Through the use of a magnet in the tip of the probe (e.g., where the transducer is located in FIG. 1, position 2) and external magnets, a flexible x-ray or beta radiation probe could be stereotactically navigated and positioned interior of the eye so that the direction and distance from the retina of the radiation source may be controlled. (See, e.g. U.S. Pat. No. 6,755,816 to Stereotaxis, Inc. of St. Louis, Mo., which is incorporated herein by reference.) The radiation probe is inserted into the eye and the device is activated. The magnets can be alternately energized in a way to move the probe so that the x-ray or beta radiation field sweeps across the lesion. The magnets may be controlled by a computer which has been pre-programmed with the desired treatment planning strategy. The sweeping across the retina can deliver different doses to different areas of the target depending upon the surgeon's assessment of the dose required to treat the underlying disease.

The low energy x-ray radiation can be blocked by a thin layer of high density metal 80, as shown in FIG. 19. Additionally, the low energy x-ray radiation may be shaped by the geometry of the anode 82 and/or cathode as shown in FIGS. 20A-C. For example, if the anode 82 of the x-ray emitter is hemispherical (FIG. 20A), x-ray radiation will be emitted around the tip of the emitter across a 180° arc (when viewed from the side). If the anode 82 has a flat shape (FIG. 20B or FIG. 20C), x-ray will be emitted substantially "longitudinally" out of the end of the emitter. The focal x-ray beam can be specifically directed at small portions of the target tissue. This selective approach toward treating areas of the retina can be especially useful when protecting non-target tissues.

Another method for protecting the non-target tissue from undue exposure to radiation is to more accurately define the boundaries of the target tissue. Pre-treatment diagnostic tests, such as color fundus photography and fluorescein angiography, provide a way to visualize the specific boundaries of the AMD lesion. Then, the focal nature of the dose distribution permits the surgeon to specifically target lesions or parts of lesions, rather than generically dosing the retina.

A color fundus photograph provides a picture or image of the retina showing similar anatomical features to what the surgeon sees through the surgical microscope. From a color fundus photograph, the surgeon can see drusen, major retinal blood vessels and other features. However, it is difficult to visualize the extent of the AMD lesion and leakage from these photographs (and during surgery).

To view the extent of the AMD lesion and leakage, a radio opaque dye is intravenously injected into the patient. As the dye circulates through the bloodstream and eventually reaches the retinal circulation, a photographer turns on an x-ray and captures frames of the dye as it perfuses the retinal and choroidal circulation. These x-ray images show boundaries of the AMD leakage that are not visible with fundus photography.

Using Imagenet software prior to surgery, the lesion boundaries can be located with respect to anatomy that can be visualized with the microscope, such as blood vessels, blood vessel branches, and the optic disc. With this information, a treatment planning strategy can be developed that includes determining, e.g., the spacing of the probe from the target tissue, the dwell time for the radiation source, the location of the center of the radiation source, and/or the type of shaping filter or window to use during surgery.

The radiation dose rate is inversely proportional to the square of the distance between the source and the target, and the dose field broadens with increasing separation between the source and the target. These features of the radiation physics may be used to control the shape of the dose distribution. In collaboration with the compliant balloon discussed above, the dose distribution could be modified to specifically match the AMD lesion. Specifically, the extent of the lesion can be measured. A compliant balloon can be designed to provide a predetermined spacing of the radiation source for a given inflation volume. Thus, based upon the size of the lesion, the inflation volume to provide the designed spacing of the radiation source to provide a therapeutic radiation dose will be known, and the balloon can be inflated to that volume.

As set forth in our co-pending applications referenced above, there is a therapeutic range of doses which have the desired treatment effect on the target tissue without undue side effects. Doses below the therapeutic range are not sufficient to halt the CNV leakage. Doses above the therapeutic range halt the CNV leakage, but may cause side effects that make the treatment risk outweigh the treatment benefit. The therapeutic range is unique to intraocular brachytherapy with ionizing radiation. The therapeutic range would likely vary with other energy sources or delivery means. The therapeutic range for Beta radiation is approximately 7-50 Gy (measured at the CNV). The preferred dose lies somewhere between 10 Gy and 30 Gy.

Combination Therapies and/or Re-Treatment of Target Tissue

It may be advantageous to treat macular degeneration with the non-ionizing radiation in combination with other therapeutic substances that are currently in use or under development. For example, certain pharmaceutical substances are currently under development that act upon the vascular endothelial growth factor (VEGF) cascade. VEGF's are vasodialating and vasoproliferative. The vasodilation feature results in leaky vessel walls while the vasoproliferation feature results in the formation of new blood vessels. Anti-VEGF pharmaceuticals, such as Macugen®, Avastin®, and Lucentis®, bind to VEGF, thereby preventing vasodilation and vasoproliferation, and halting the CNV leakage.

Clinical trials with the anti-VEGF pharmaceutical Lucentis® have shown it to be efficacious not only in slowing the effects of vasodilation and vasoprofliferation, but in also reducing leakage very soon after injection. However, the effects are not permanent, and the drug must be injected monthly to obtain the maximum efficacy. In contrast, because radiation treatment works by interfering with cell division at the DNA level, the effects of radiation treatment are not expected to be immediate. Indeed, clinical trials show a decrease in visual acuity at one week post-op, a small increase at four weeks, and a bigger increase at two months. Therefore, a combination treatment with an anti-VEGF and radiation therapy may have an early effect, mainly due to the pharmaceutical, and a late effect, mainly due to the radiation therapy.

The time interval between the radiation treatment and the treatment with the anti-VEGF is preferably two weeks or less, more preferably five days or less, and even more preferably four hours or less. The most preferred time interval would be 15 minutes or less. That is, both the radiation and the anti-VEGF are administered during the same procedure. This could be done with a single device in which the cannula or probe for delivering the radiation dose also includes a separate lumen through which the anti-VEGF can be injected, as shown and described in the co-pending applications referenced above. The radiation source could be either a beta emitter or a miniature x-ray emitter, which preferably delivers a radiation dose to the target tissue of from 20 to 30 Gy at a dose rate of 5 to 30 cGy/sec, and more preferably at a dose rate of 8 to 15 cGy/sec. The anti-VEGF pharmaceuticals could be delivered prior to, after, or both prior to and after brachytherapy.

A subsequent dose of an anti-VEGF pharmaceutical may also be administered to the target tissue intraocularly to enhance the complimentary effects of the combination therapy. The second dose may be given from two to eight weeks after the first dose, preferably three to five weeks after the first dose, and more preferably 25 to 35 days after the first dose.

Other therapeutic agents or modalities may also be used in combination with radiation for the treatment of macular degeneration. By way of example and not limitation, these may include, in any combination, one or more of small interfering RNA ("siRNA"), photodynamic therapy ("PDT"—typically with verteporfin as the photosensitizing agent), corticosteroids (such as triamcinolone acetonide and dexamethasone), angiostatic steroids (such as anecortave acetate), implants of encapsulated human ciliary neurotrophic factor ("CNTF"—NTC-201), VEGF Traps, dietary supplements (e.g., docosahexaenoic acid), anti-inflammatory medicines (e.g., infliximab, sirolimus, decliziumab or ketorolac tromethamine), interferon, antimetabolite drugs (e.g., methotrexate), squalamine lactate (an aminosterol), ruboxistaurin mesylate (a protein kinase C beta inhibitor), fluocinolon acetonide implants, monoclonal antibodies (e.g., Sphingomab), and anti-oxidants. Such pharmaceuticals may be administered in a wide variety of ways, such as intravitreously, intravenously, subcutaneously (by injection), orally, topically (including eye drops), and by implantation.

Re-irradiation of the target tissue may also be indicated. The tissue response to radiation is proportional to the dose delivered, and there are four general tissue responses to the radiation. At low doses (below the therapeutic threshold), there is little or no lasting tissue response. At doses above the therapeutic threshold, but below the toxicity threshold, the desired therapeutic effect is attained. At doses above the toxicity threshold, long-term fibrosis and scarring can occur. At doses significantly above the therapeutic threshold, acute necrosis and scarring will occur.

Fractionation studies with external radiation therapy for AMD have not shown any appreciable benefit. However, re-treatment of patients that show recurrence of AMD with radiation may provide a benefit without exceeding the threshold for toxicity. The literature provides some evidence of an accumulation effect in the tissue of radiation over multiple treatments (i.e. previously irradiated tissue may be more sensitive than virgin tissue to new radiation treatments). If this theory is proven, it may affect the first, second, and third dose strategies. Additionally, the tissue may recover with time between radiation treatments.

What is claimed:

1. A method of positioning a device for local delivery of radiation to intraocular sub-retinal target tissue a pre-determined space relative to the target tissue comprising:
providing a device comprising a cannula sized for insertion into an eye and having a proximal end and a distal end; a radiation-emitting source adapted to be located in the distal end of the cannula; and an ultrasound transducer located in the distal end of the cannula adapted to directionally emit ultrasonic radiation toward the target tissue;
calibrating the ultrasound transducer in accordance with a predetermined spacing for the distal end of the cannula from the sub-retinal target tissue so as to generate a signal when the predetermined spacing is achieved;
introducing the cannula into an eye through an access site on the eye; and
moving the distal end of the cannula toward the sub-retinal target tissue until the signal generated by the ultrasound transducer is perceived by a user.

2. The method of claim 1 wherein the ultrasound transducer is located in the distal end of the cannula proximal to the radiation-emitting source.

3. The method of claim 1 wherein the ultrasound transducer is located in the distal end of the cannula distal to the radiation-emitting source.

4. The method of claim 1 wherein the signal generated by the ultrasound transducer is an audible signal.

5. The method of claim 1 wherein the signal generated by the ultrasound transducer is a visual signal.

6. A method of positioning a first cannula within an eye for delivery of a therapeutic treatment to a target tissue within the eye comprising:
introducing the first cannula into the eye through an access site on the eye;
introducing a second cannula into the eye through an access site on the eye, the second cannula including an ultrasound transducer;
positioning the distal end of the first cannula between the ultrasound transducer associated with the second cannula and the target tissue; and
moving the distal portion of the first cannula toward the target tissue until a predetermined spacing between the distal end of the first cannula and the target tissue is achieved, at which time a signal is generated by the ultrasound transducer.

7. The method of claim 6 wherein the signal generated by the ultrasound transducer is an audible signal.

8. The method of claim 6 wherein the signal generated by the ultrasound transducer is a visual signal.

* * * * *